US012688926B2

(12) United States Patent
Bao et al.

(10) Patent No.: US 12,688,926 B2
(45) Date of Patent: Jul. 21, 2026

(54) METHODS AND SYSTEMS FOR NEW DATA STORAGE AND MANAGEMENT SCHEME FOR MEDICAL IMAGING SOLUTIONS

(71) Applicant: GE Precision Healthcare LLC, Waukesha, WI (US)

(72) Inventors: Yongjian Bao, Vernon Hills, IL (US); Vijay Arlagadda, Hoffman Estates, IL (US); Arun Viswanath, Barrington Hills, IL (US); Jouke Numan, Austerlitz (NL)

(73) Assignee: GE Precision Healthcare LLC, Waukesha, WI (US)

( * ) Notice: Subject to any disclaimer, the term of this patent is extended or adjusted under 35 U.S.C. 154(b) by 0 days.

(21) Appl. No.: 19/060,410

(22) Filed: Feb. 21, 2025

(65) Prior Publication Data

US 2025/0266149 A1     Aug. 21, 2025

Related U.S. Application Data

(63) Continuation of application No. 17/219,348, filed on Mar. 31, 2021, now abandoned.

(51) Int. Cl.
*G16H 30/20* (2018.01)
*G16H 40/63* (2018.01)
*G16H 40/67* (2018.01)

(52) U.S. Cl.
CPC ............ *G16H 30/20* (2018.01); *G16H 40/63* (2018.01); *G16H 40/67* (2018.01)

(58) Field of Classification Search
CPC ......... G16H 30/20; G16H 40/67; G16H 40/63
See application file for complete search history.

(56) References Cited

U.S. PATENT DOCUMENTS

| | | | | |
|---|---|---|---|---|
| 9,349,186 | B2 * | 5/2016 | Liu | .......................... G06T 7/11 |
| 2005/0078863 | A1 * | 4/2005 | Ito | ....................... H04N 25/671 |
| | | | | 382/254 |

(Continued)

OTHER PUBLICATIONS

EP application 22781813.5 filed Sep. 19, 2023—extended Search Report issued Feb. 4, 2025; 10 pages.

(Continued)

*Primary Examiner* — Courtney Harmon

(57) ABSTRACT

Systems and methods are provided for new data storage and management scheme for medical imaging solutions. Medical data storage and management processes, including at least a separation process and a recovery process, may be applied to a medical dataset. The separation process includes identifying blob data elements in the medical dataset, moving data of the identified blob data elements into corresponding separated data objects, and generating data for indicating the moving of data of and for tracking location of moved data of the identified blob data elements. The recovery process includes identifying removed blob data elements in a separated medical dataset, with data of the identified removed blob data elements moved into corresponding separated data objects, and for each identified removed blob data element determining, based on corresponding separation data, location of a corresponding separated data object; and retrieving, based on determined location, data of the removed blob data element.

20 Claims, 9 Drawing Sheets

(56) References Cited

U.S. PATENT DOCUMENTS

| | | | | |
|---|---|---|---|---|
| 2013/0089257 A1* | 4/2013 | Kim | ...................... | G06T 1/0028 |
| | | | | 382/190 |
| 2013/0311521 A1 | 11/2013 | Gene | | |
| 2016/0148375 A1* | 5/2016 | Oh | ......................... | A61B 5/743 |
| | | | | 382/131 |
| 2019/0029623 A1* | 1/2019 | Kunio | .................. | A61B 8/0891 |
| 2020/0160985 A1* | 5/2020 | Kusuma | ................. | G16H 30/40 |

OTHER PUBLICATIONS

Pyarali et al: "Design and Performance of an Object-Oriented Framework for High-Speed Electronic Medical Imaging" Computing Systems, Usenix Association, Berkeley, CA, US, vol. 9 n. 4, Jan. 1, 1996, pp. 331-375, XP197949A.

* cited by examiner

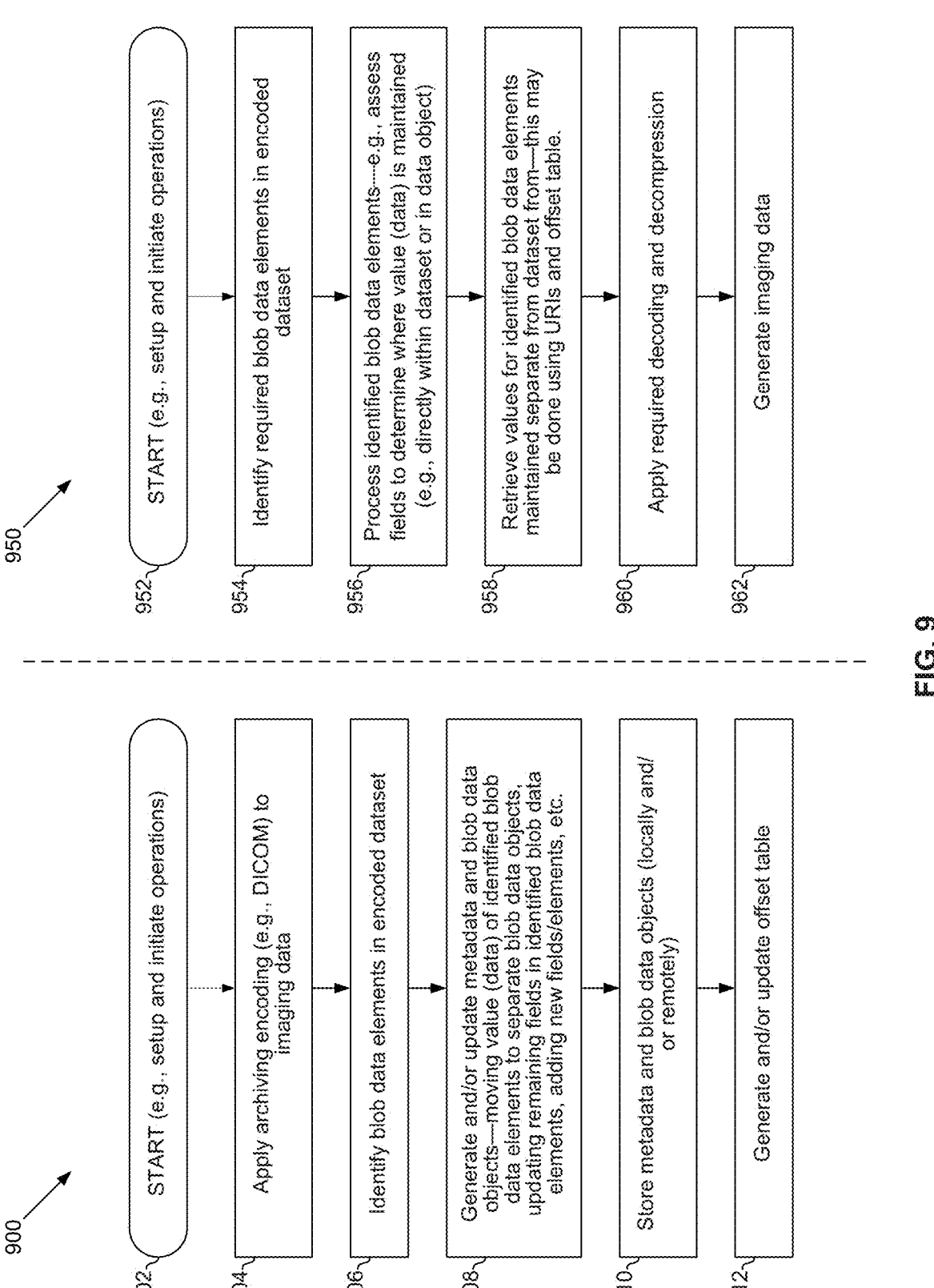

952 START (e.g., setup and initiate operations)

954 Identify required blob data elements in encoded dataset

956 Process identified blob data elements—e.g., assess fields to determine where value (data) is maintained (e.g., directly within dataset or in data object)

958 Retrieve values for identified blob data elements maintained separate from dataset from—this may be done using URIs and offset table.

960 Apply required decoding and decompression

962 Generate imaging data

900

902 START (e.g., setup and initiate operations)

904 Apply archiving encoding (e.g., DICOM) to imaging data

906 Identify blob data elements in encoded dataset

908 Generate and/or update metadata and blob data objects—moving value (data) of identified blob data elements to separate blob data objects, updating remaining fields in identified blob data elements, adding new fields/elements, etc.

910 Store metadata and blob data objects (locally and/or remotely)

912 Generate and/or update offset table

METHODS AND SYSTEMS FOR NEW DATA STORAGE AND MANAGEMENT SCHEME FOR MEDICAL IMAGING SOLUTIONS

CROSS-REFERENCE TO RELATED APPLICATIONS

This application is a continuation of and claims priority to U.S. patent application Ser. No. 17/219,348, titled "METHODS AND SYSTEMS FOR NEW DATA STORAGE AND MANAGEMENT SCHEME FOR MEDICAL IMAGING SOLUTIONS," filed Mar. 31, 2021, the contents of which are incorporated by reference herein.

FIELD

Aspects of the present disclosure relate to medical imaging solutions. More specifically, certain embodiments relate to methods and systems for new data storage and management scheme for medical imaging solutions.

BACKGROUND

Various medical imaging techniques may be used, such as in imaging organs and soft tissues in a human body. Examples of medical imaging techniques include ultrasound imaging, computed tomography (CT) scans, magnetic resonance imaging (MRI), etc. The manner by which images are generated during medical imaging depends on the particular technique.

For example, ultrasound imaging uses real time, non-invasive high frequency sound waves to produce ultrasound images, typically of organs, tissues, objects (e.g., fetus) inside the human body. Images produced or generated during medical imaging may be two-dimensional (2D), three-dimensional (3D), and/or four-dimensional (4D) images (essentially real-time/continuous 3D images). During medical imaging, imaging datasets (including, e.g., volumetric imaging datasets during 3D/4D imaging) are acquired and used in generating and rendering corresponding images (e.g., via a display) in real-time.

In some instances, there may be a need to storage imaging data generated during medical imaging. Storage of such imaging data may pose certain challenges, particularly with respect to use of resources in the medical images systems and/or systems where this imaging data is used.

Further limitations and disadvantages of conventional and traditional approaches will become apparent to one of skill in the art, through comparison of such systems with some aspects of the present disclosure, as set forth in the remainder of the present application with reference to the drawings.

BRIEF SUMMARY

System and methods are provided for new data storage and management scheme for medical imaging solutions, substantially as shown in and/or described in connection with at least one of the figures, as set forth more completely in the claims.

These and other advantages, aspects and novel features of the present disclosure, as well as details of one or more illustrated example embodiments thereof, will be more fully understood from the following description and drawings.

BRIEF DESCRIPTION OF THE DRAWINGS

FIG. 9 illustrates flowcharts of example separation and recovery processes based on the new data storage and management scheme in accordance with the present disclosure.

DETAILED DESCRIPTION

Figure 1:
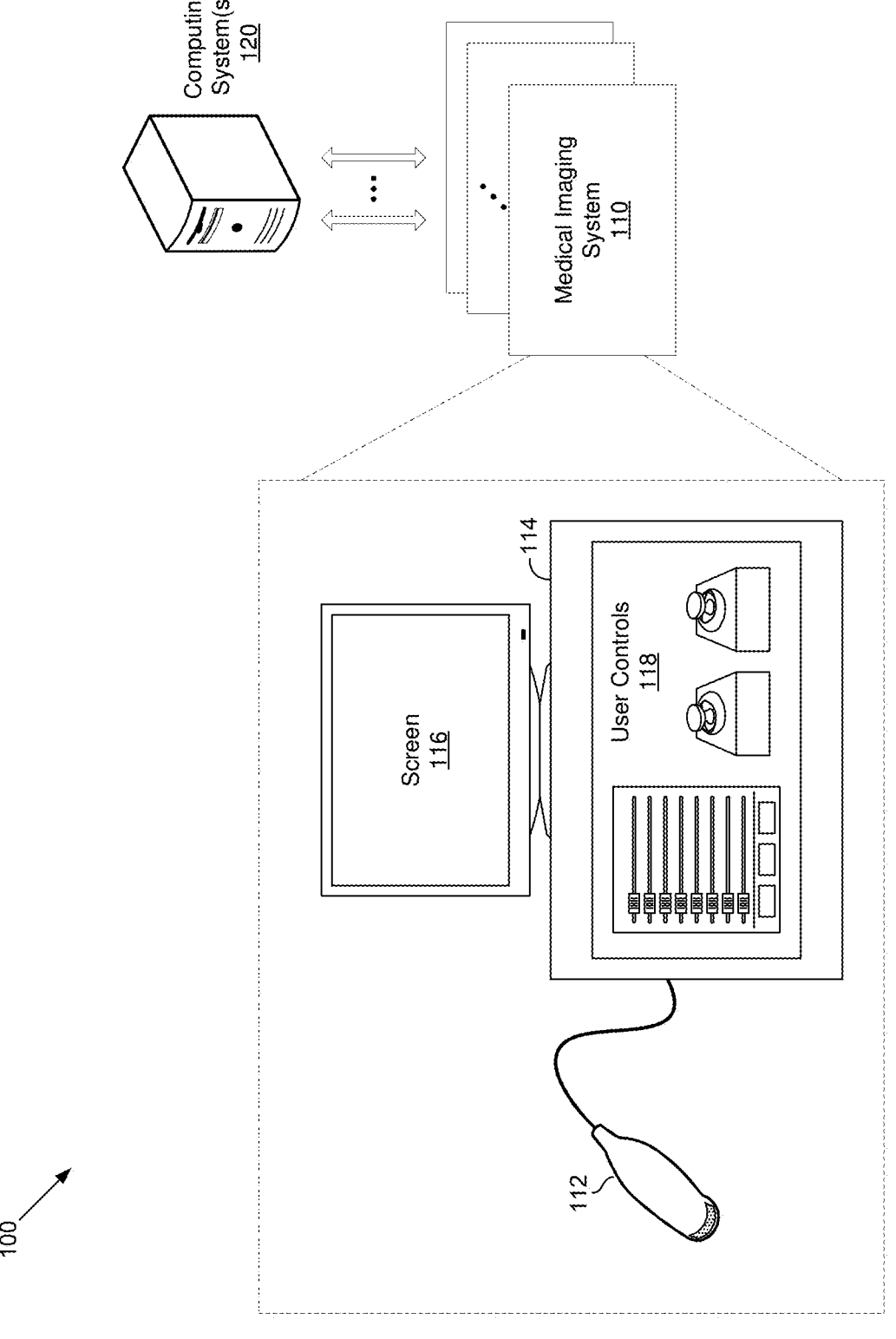
FIG. 1 illustrates an example medical imaging arrangement that may be configured for supporting new data storage and management scheme for medical imaging solutions.

Certain implementations in accordance with the present disclosure may be directed to new data storage and management scheme for medical imaging solutions. In particular, the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand-alone programs, may be incorporated as subroutines in an operating system, may be functions in an installed software package, and the like. It should be understood that the various embodiments are not limited to the arrangements and instrumentality shown in the drawings. It should also be understood that the embodiments may be combined, or that other embodiments may be utilized and that structural, logical and electrical changes may be made without departing from the scope of the various embodiments. The following detailed description is, therefore, not to be taken in a limiting sense, and the scope of the present disclosure is defined by the appended claims and their equivalents.

As used herein, an element or step recited in the singular and preceded with the word "a" or "an" should be understood as not excluding plural of said elements or steps, unless such exclusion is explicitly stated. Furthermore, references to "an exemplary embodiment," "various embodiments," "certain embodiments," "a representative embodiment," and the like are not intended to be interpreted as excluding the existence of additional embodiments that also incorporate the recited features. Moreover, unless explicitly stated to the contrary, embodiments "comprising," "including," or "having" an element or a plurality of elements having a particular property may include additional elements not having that property.

Also as used herein, the term "image" broadly refers to both viewable images and data representing a viewable image. However, many embodiments generate (or are configured to generate) at least one viewable image. In addition, as used herein, the phrase "image" is used to refer to an ultrasound mode such as B-mode (2D mode), M-mode, three-dimensional (3D) mode, CF-mode, PW Doppler, CW Doppler, MGD, and/or sub-modes of B-mode and/or CF such as Shear Wave Elasticity Imaging (SWEI), TVI, Angio, B-flow, BMI, BMI_Angio, and in some cases also MM, CM, TVD where the "image" and/or "plane" includes a single beam or multiple beams.

In addition, as used herein, the phrase "pixel" also includes embodiments where the data is represented by a "voxel." Thus, both the terms "pixel" and "voxel" may be used interchangeably throughout this document.

Furthermore, the term processor or processing unit, as used herein, refers to any type of processing unit that can carry out the required calculations needed for the various embodiments, such as single or multi-core: CPU, Accelerated Processing Unit (APU), Graphics Board, DSP, FPGA, ASIC, or a combination thereof.

It should be noted that various embodiments described herein that generate or form images may include processing for forming images that in some embodiments includes beamforming and in other embodiments does not include beamforming. For example, an image can be formed without beamforming, such as by multiplying the matrix of demodulated data by a matrix of coefficients so that the product is the image, and wherein the process does not form any "beams". In addition, forming of images may be performed using channel combinations that may originate from more than one transmit event (e.g., synthetic aperture techniques).

Figure 2:
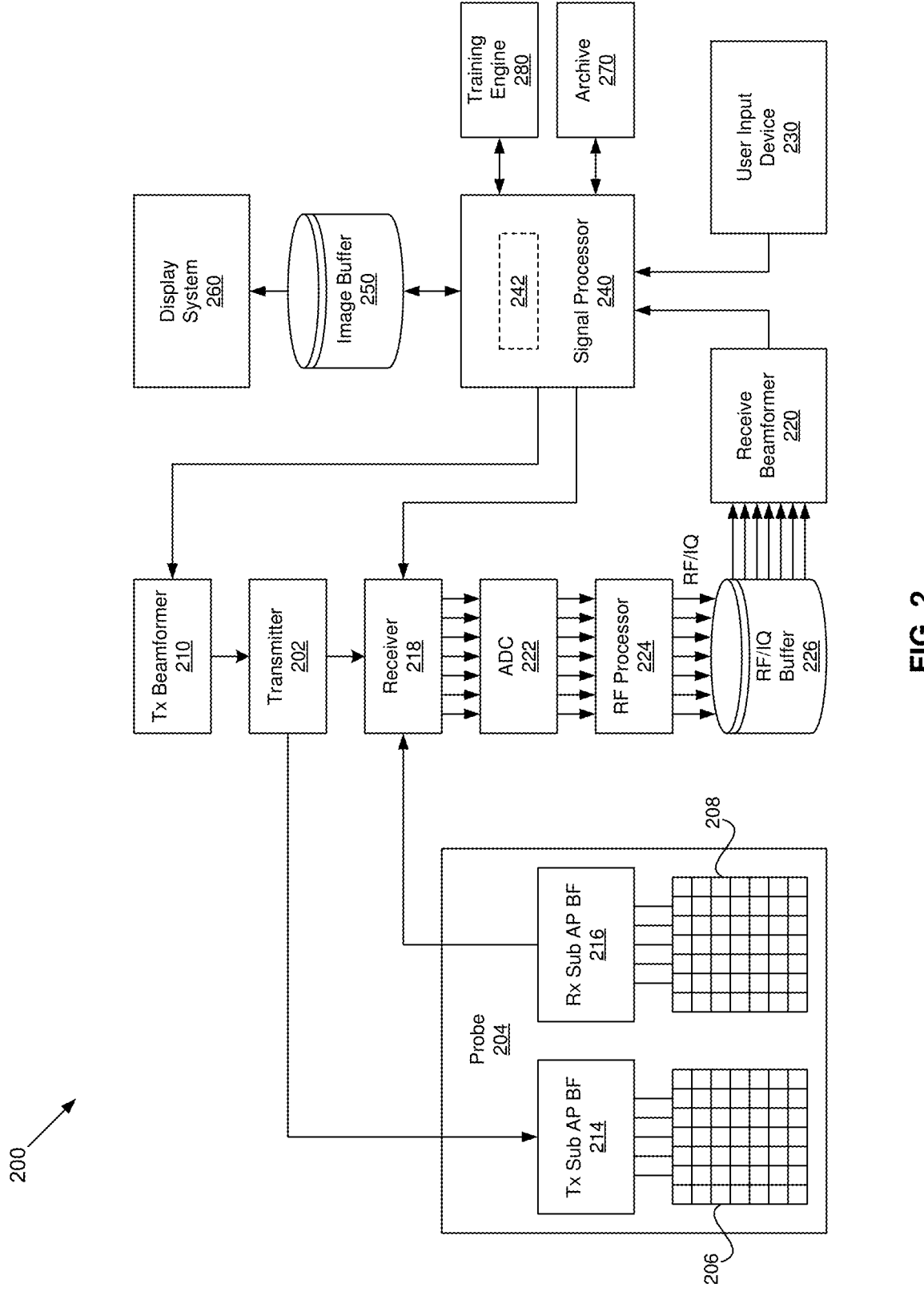
FIG. 2 illustrates an example ultrasound system that may be configured for supporting new data storage and management scheme for medical imaging solutions.

In various embodiments, processing to form images, including beamforming, is performed in software, firmware, hardware, or a combination thereof. One example implementation of an ultrasound system having a software beamformer architecture formed in accordance with various embodiments as illustrated in FIG. 2.

FIG. 1 illustrates an example medical imaging arrangement that may be configured for supporting utilizing histogram views for improved visualization of three-dimensional (3D) medical images. Shown in FIG. 1 is an example setup 100 that comprises one or more medical imaging systems 110 and one or more computing systems 120.

The medical imaging system 110 comprise suitable hardware, software, or a combination thereof, for supporting medical imaging—that is enabling obtaining data used in generating and/or rendering images during medical imaging exams. Examples of medical imaging include ultrasound imaging, computed tomography (CT) scans, magnetic resonance imaging (MRI), etc. This may entail capturing of particular type of data, in particular manner, which may in turn be used in generating data for the images. For example, the medical imaging system 110 may be an ultrasound imaging system, configured for generating and/or rendering ultrasound images. An example implementation of an ultrasound system, which may correspond to the medical imaging system 110, is described in more detail with respect to FIG. 2.

As shown in FIG. 1, the medical imaging system 110 may comprise a scanner device 112, which may be portable and movable, and a display/control unit 114. The scanner device 112 may be configured for generating and/or capturing particular type of imaging signals (and/or data corresponding thereto), such as by being moved over a patient's body (or part thereof), and may comprise suitable circuitry for performing and/or supporting such functions. The scanner device 112 may be an ultrasound probe, MRI scanner, CT scanner, or any suitable imaging device. For example, where the medical imaging system 110 is an ultrasound system, the scanner device 112 may emit ultrasound signals and capture echo ultrasound images.

The display/control unit 114 may be configured for displaying images (e.g., via a screen 116). In some instances, the display/control unit 114 may further be configured for generating the displayed images, at least partly. Further, the display/control unit 114 may also support user input/output. For example, the display/control unit 114 may provide (e.g., via the screen 116), in addition to the images, user feedback (e.g., information relating to the system, functions thereof, settings thereof, etc.). The display/control unit 114 may also support user input (e.g., via user controls 118), such as to allow controlling of the medical imaging. The user input may be directed to controlling display of images, selecting settings, specifying user preferences, requesting feedback, etc.

In some implementation, the medical imaging system 110 may also incorporate additional and dedicated computing resources, such as the one or more computing systems 120. In this regard, each computing system 120 may comprise suitable circuitry, interfaces, logic, and/or code for processing, storing, and/or communication data. The computing system 120 may be dedicated equipment configured particularly for use in conjunction with medical imaging, or it may be a general purpose computing system (e.g., personal computer, server, etc.) set up and/or configured to perform the operations described hereinafter with respect to the computing system 120. The computing system 120 may be configured to support operations of the medical imaging systems 110, as described below. In this regard, various functions and/or operations may be offloaded from the imaging systems. This may be done to streamline and/or centralize certain aspects of the processing, to reduce cost—e.g., by obviating the need to increase processing resources in the imaging systems.

The computing systems 120 may be set up and/or arranged for use in different ways. For example, in some implementations a single computing system 120 may be used; in other implementations multiple computing systems 120, either configured to work together (e.g., based on distributed-processing configuration), or separately, with each computing system 120 being configured to handle particular aspects and/or functions, and/or to process data only for particular medical imaging systems 110. Further, in some implementations, the computing systems 120 may be local (e.g., co-located with one or more medical imaging systems 110, such within the same facility and/or same local network); in other implementations, the computing systems 120 may be remote and thus can only be accessed via remote connections (e.g., via the Internet or other available remote access techniques). In a particular implementation, the computing systems 120 may be configured in cloud-based manner, and may be accessed and/or used in substantially similar way that other cloud-based systems are accessed and used.

Once data is generated and/or configured in the computing system 120, the data may be copied and/or loaded into the medical imaging systems 110. This may be done in different ways. For example, the data may be loaded via directed connections or links between the medical imaging systems 110 and the computing system 120. In this regard, communications between the different elements in the setup 100 may be done using available wired and/or wireless connections, and/or in accordance any suitable communication (and/or networking) standards or protocols. Alternatively, or additionally, the data may be loaded into the medical imaging systems 110 indirectly. For example, the data may be stored into suitable machine readable media (e.g., flash card, etc.), which are then used to load the data into the medical imaging systems 110 (on-site, such as by users of the systems (e.g., imaging clinicians) or authorized personnel), or the data may be downloaded into local communication-capable electronic devices (e.g., laptops, etc.), which are then used on-site (e.g., by users of the systems or authorized personnel) to upload the data into the medical imaging systems 110, via direct connections (e.g., USB connector, etc.).

In operation, the medical imaging system 110 may be used in generating and presenting (e.g., rendering or displaying) images during medical exams, and/or in supporting user input/output in conjunction therewith. The images may be 2D, 3D, and/or 4D images. The particular operations or functions performed in the medical imaging system 110 to facilitate the generating and/or presenting of images depends on the type of system—that is, the manner by which the data corresponding to the images is obtained and/or generated. For example, in ultrasound imaging, the data is based on emitted and echo ultrasound signals, as described in more detail with respect to FIG. 2.

In accordance with the present disclosure, medical imaging systems (e.g., the medical imaging system 110) may be configured to support new data storage and management scheme for medical imaging solutions. In this regard, medical data, in particular diagnostic imaging data, may be archived as "data blobs" in a multi-tier, hierarchical storage system, with a small record of metadata for each of the data blobs stored in a relational database (referred to hereinafter as "index"). The metadata record may contain a file path where the corresponding data blob may be located. Such scheme has been employed in various medical data archiving systems, vendor neutral archive (VNA), picture archiving and communication system (PACS), etc. However, various challenges and issues may arise with use of existing data storage schemes and solutions based thereon.

In this regard, total volume of medical data has been steadily (and even exponentially) increasing, especially with various advanced medical examinations and imaging procedures. Such increase is creating particular challenges with traditional data storage scheme(s). This is particularly problematic due to inherent inefficiencies with the traditional data storage scheme(s). For example, data access is supported on the whole data blob level, even though only partial content may be needed and/or requested in many workloads. In addition, the whole data blob may need to be re-written if any piece of information inside is modified. Further, the whole data blob may be handled in the same storage mechanism, despite of the fact that different pieces inside may lead to different, more efficient mechanisms.

Accordingly, in various implementations in accordance with the present disclosure, modified data storage scheme may be used for improving access to and use of medical data, particularly data archived as data blobs. In particular, in accordance with the new data storage scheme, a whole data blob may be separated into metadata and blob data parts. In this regard, as noted above, traditional data storage scheme(s) may typically rely on indexed databases to access metadata of stored data objects, which may be restricted by the index content for metadata access, as well as suffer from performance shortcoming when massive metadata fetch (and/or data updates based thereon) may be demanded.

The proposed data scheme, addresses such issues, however, particularly by separating medical data objects into metadata and blob data parts, while additionally bi-directionally referencing them to each other with well-defined, standard format and high data integrity protection. This may allow for separate metadata workloads and blob data workloads in data storage and management system, to optimize resource utilization, dramatically improve operation performance, and flexible system architecture. In addition, new application programming interface (API) may be used for separate access to metadata and blob data. Further, rich metadata information may be made available to applications without updating data index scheme. An example implementation based on Digital Imaging and Communications in Medicine (DICOM) is illustrated and described with respect to FIGS. 3-4 below. Nonetheless, it should be understood that the disclosure is not limited to DICOM based implementations.

FIG. 2 illustrates an example ultrasound system that may be configured for supporting utilizing histogram views for improved visualization of three-dimensional (3D) medical images. Shown in FIG. 2 is an ultrasound system 200.

The ultrasound system 200 may be configured for providing ultrasound imaging, and as such may comprise suitable circuitry, interfaces, logic, and/or code for performing and/or supporting ultrasound imaging related functions. The ultrasound system 200 may correspond to the medical imaging system 110 of FIG. 1. The ultrasound system 200 comprises, for example, a transmitter 202, an ultrasound probe 204, a transmit beamformer 210, a receiver 218, a receive beamformer 220, a RF processor 224, a RF/IQ buffer 226, a user input module 230, a signal processor 240, an image buffer 250, a display system 260, an archive 270, and a training engine 280.

The transmitter 202 may comprise suitable circuitry, interfaces, logic, and/or code that may be operable to drive an ultrasound probe 204. The ultrasound probe 204 may comprise a two dimensional (2D) array of piezoelectric elements. The ultrasound probe 204 may comprise a group of transmit transducer elements 206 and a group of receive transducer elements 208, that normally constitute the same elements. In certain embodiment, the ultrasound probe 204 may be operable to acquire ultrasound image data covering at least a substantial portion of an anatomy, such as the heart, a blood vessel, or any suitable anatomical structure.

The transmit beamformer 210 may comprise suitable circuitry, interfaces, logic, and/or code that may be operable to control the transmitter 202 which, through a transmit sub-aperture beamformer 214, drives the group of transmit transducer elements 206 to emit ultrasonic transmit signals into a region of interest (e.g., human, animal, underground cavity, physical structure and the like). The transmitted ultrasonic signals may be back-scattered from structures in the object of interest, like blood cells or tissue, to produce echoes. The echoes are received by the receive transducer elements 208.

The group of receive transducer elements 208 in the ultrasound probe 204 may be operable to convert the received echoes into analog signals, undergo sub-aperture beamforming by a receive sub-aperture beamformer 216 and are then communicated to a receiver 218. The receiver 218 may comprise suitable circuitry, interfaces, logic, and/or code that may be operable to receive the signals from the receive sub-aperture beamformer 216. The analog signals may be communicated to one or more of the plurality of A/D converters 222.

The plurality of A/D converters 222 may comprise suitable circuitry, interfaces, logic, and/or code that may be operable to convert the analog signals from the receiver 218 to corresponding digital signals. The plurality of A/D converters 222 are disposed between the receiver 218 and the RF processor 224. Notwithstanding, the disclosure is not limited in this regard. Accordingly, in some embodiments, the plurality of A/D converters 222 may be integrated within the receiver 218.

The RF processor 224 may comprise suitable circuitry, interfaces, logic, and/or code that may be operable to demodulate the digital signals output by the plurality of A/D converters 222. In accordance with an embodiment, the RF processor 224 may comprise a complex demodulator (not shown) that is operable to demodulate the digital signals to form I/Q data pairs that are representative of the corresponding echo signals. The RF or I/Q signal data may then be communicated to an RF/IQ buffer 226. The RF/IQ buffer 226 may comprise suitable circuitry, interfaces, logic, and/or code that may be operable to provide temporary storage of the RF or I/Q signal data, which is generated by the RF processor 224.

The receive beamformer 220 may comprise suitable circuitry, interfaces, logic, and/or code that may be operable to perform digital beamforming processing to, for example, sum the delayed channel signals received from RF processor 224 via the RF/IQ buffer 226 and output a beam summed signal. The resulting processed information may be the beam summed signal that is output from the receive beamformer 220 and communicated to the signal processor 240. In accordance with some embodiments, the receiver 218, the plurality of A/D converters 222, the RF processor 224, and the beamformer 220 may be integrated into a single beamformer, which may be digital. In various embodiments, the ultrasound system 200 comprises a plurality of receive beamformers 220.

The user input device 230 may be utilized to input patient data, scan parameters, settings, select protocols and/or templates, interact with an artificial intelligence segmentation processor to select tracking targets, and the like. In an example embodiment, the user input device 230 may be operable to configure, manage and/or control operation of one or more components and/or modules in the ultrasound system 200. In this regard, the user input device 230 may be operable to configure, manage and/or control operation of the transmitter 202, the ultrasound probe 204, the transmit beamformer 210, the receiver 218, the receive beamformer 220, the RF processor 224, the RF/IQ buffer 226, the user input device 230, the signal processor 240, the image buffer 250, the display system 260, and/or the archive 270.

For example, the user input device 230 may include button(s), rotary encoder(s), a touchscreen, motion tracking, voice recognition, a mouse device, keyboard, camera and/or any other device capable of receiving user directive(s). In certain embodiments, one or more of the user input devices 230 may be integrated into other components, such as the display system 260 or the ultrasound probe 204, for example.

As an example, user input device 230 may include a touchscreen display. As another example, user input device 230 may include an accelerometer, gyroscope, and/or magnetometer attached to and/or integrated with the probe 204 to provide gesture motion recognition of the probe 204, such as to identify one or more probe compressions against a patient body, a pre-defined probe movement or tilt operation, or the like. In some instances, the user input device 230 may include, additionally or alternatively, image analysis processing to identify probe gestures by analyzing acquired image data. In accordance with the present disclosure, the user input and functions related thereto may be configured to support use of new data storage scheme, as described in this disclosure. For example, the user input device 230 may be configured to support receiving user input directed at triggering and managing (where needed) application of separation process, as described herein, and/or to provide or set parameters used in performing such process. Similarly, the user input device 230 may be configured to support receiving user input directed at triggering and managing (where needed) application of the recovery process, as described herein, and/or to provide or set parameters used in performing such process.

The signal processor 240 may comprise suitable circuitry, interfaces, logic, and/or code that may be operable to process ultrasound scan data (i.e., summed IQ signal) for generating ultrasound images for presentation on a display system 260. The signal processor 240 is operable to perform one or more processing operations according to a plurality of selectable ultrasound modalities on the acquired ultrasound scan data. In an example embodiment, the signal processor 240 may be operable to perform display processing and/or control processing, among other things. Acquired ultrasound scan data may be processed in real-time during a scanning session as the echo signals are received. Additionally or alternatively, the ultrasound scan data may be stored temporarily in the RF/IQ buffer 226 during a scanning session and processed in less than real-time in a live or off-line operation. In various embodiments, the processed image data can be presented at the display system 260 and/or may be stored at the archive 270. The archive 270 may be a local archive, a Picture Archiving and Communication System (PACS), or any suitable device for storing images and related information.

The signal processor 240 may be one or more central processing units, microprocessors, microcontrollers, and/or the like. The signal processor 240 may be an integrated component, or may be distributed across various locations, for example. The signal processor 240 may be configured for receiving input information from the user input device 230 and/or the archive 270, generating an output displayable by the display system 260, and manipulating the output in response to input information from the user input device 230, among other things. The signal processor 240 may be capable of executing any of the method(s) and/or set(s) of instructions discussed herein in accordance with the various embodiments, for example.

The ultrasound system 200 may be operable to continuously acquire ultrasound scan data at a frame rate that is suitable for the imaging situation in question. Typical frame rates range from 20-220 but may be lower or higher. The acquired ultrasound scan data may be displayed on the display system 260 at a display-rate that can be the same as the frame rate, or slower or faster. The image buffer 250 is included for storing processed frames of acquired ultrasound scan data that are not scheduled to be displayed immediately. Preferably, the image buffer 250 is of sufficient capacity to store at least several minutes' worth of frames of ultrasound scan data. The frames of ultrasound scan data are stored in a manner to facilitate retrieval thereof according to its order or time of acquisition. The image buffer 250 may be embodied as any known data storage medium.

In an example embodiment, the signal processor 240 may comprise a data management module 242, which comprises suitable circuitry, interfaces, logic, and/or code that may be configured to perform and/or support various functions or operations relating to, or in support of new data storage and management scheme for medical imaging solutions, as described in this disclosure.

In some implementations, the signal processor 240 (and/or components thereof, such as the data management module 242) may be configured to implement and/or use artificial intelligence and/or machine learning techniques to enhance and/or optimize imaging related functions or operations. For example, the signal processor 240 (and/or components thereof, such as the data management module 242) may be configured to implement and/or use deep learning techniques and/or algorithms, such as by use of deep neural networks (e.g., a convolutional neural network (CNN)), and/or may utilize any suitable form of artificial intelligence image analysis techniques or machine learning processing functionality, which may be configured to analyze acquired ultrasound images, such as to identify, segment, label, and track structures (or tissues thereof) meeting particular criteria and/or having particular characteristics.

In an example implementation, the signal processor 240 (and/or components thereof, such as the data management module 242) may be provided as a deep neural network, which may be made up of, for example, an input layer, an output layer, and one or more hidden layers in between the input and output layers. Each of the layers may be made up of a plurality of processing nodes that may be referred to as neurons. For example, the deep neural network may include an input layer having a neuron for each pixel or a group of pixels from a scan plane of an anatomical structure, and the output layer may have a neuron corresponding to a plurality of pre-defined structures or types of structures (or tissue(s) therein). Each neuron of each layer may perform a processing function and pass the processed ultrasound image information to one of a plurality of neurons of a downstream layer for further processing.

As an example, neurons of a first layer may learn to recognize edges of structure in the ultrasound image data. The neurons of a second layer may learn to recognize shapes based on the detected edges from the first layer. The neurons of a third layer may learn positions of the recognized shapes relative to landmarks in the ultrasound image data. The neurons of a fourth layer may learn characteristics of particular tissue types present in particular structures, etc. Thus, the processing performed by the deep neural network (e.g., convolutional neural network (CNN)) may allow for identifying biological and/or artificial structures in ultrasound image data with a high degree of probability.

In some implementations, the signal processor 240 (and/or components thereof, such as the data management module 242) may be configured to perform or otherwise control at least some of the functions performed thereby based on a user instruction via the user input device 230. As an example, a user may provide a voice command, probe gesture, button depression, or the like to issue a particular instruction, such as to initiate and/or control various aspects of the new data management scheme, including artificial intelligence (AI) based operations, and/or to provide or otherwise specify various parameters or settings relating thereto, as described in this disclosure.

The training engine 280 may comprise suitable circuitry, interfaces, logic, and/or code that may be operable to train the neurons of the deep neural network(s) of the signal processor 240 (and/or components thereof, such as the data management module 242). For example, the signal processor 240 may be trained to identify particular structures and/or tissues (or types thereof) provided in an ultrasound scan plane, with the training engine 280 training the deep neural network(s) thereof to perform some of the required functions, such as using databases(s) of classified ultrasound images of various structures.

As an example, the training engine 280 may be configured to utilize ultrasound images of particular structures to train the signal processor 240 (and/or components thereof, such as the data management module 242) with respect to the characteristics of the particular structure(s), such as the appearance of structure edges, the appearance of structure shapes based on the edges, the positions of the shapes relative to landmarks in the ultrasound image data, and the like, and/or with respect to characteristics of particular tissues (e.g., softness thereof). In various embodiments, the databases of training images may be stored in the archive 270 or any suitable data storage medium. In certain embodiments, the training engine 280 and/or training image databases may be external system(s) communicatively coupled via a wired or wireless connection to the ultrasound system 200.

In operation, the ultrasound system 200 may be used in generating ultrasonic images, including two-dimensional (2D), three-dimensional (3D), and/or four-dimensional (4D) images. In this regard, the ultrasound system 200 may be operable to continuously acquire ultrasound scan data at a particular frame rate, which may be suitable for the imaging situation in question. For example, frame rates may range from 20-70 but may be lower or higher. The acquired ultrasound scan data may be displayed on the display system 260 at a display-rate that can be the same as the frame rate, or slower or faster. An image buffer 250 is included for storing processed frames of acquired ultrasound scan data not scheduled to be displayed immediately. Preferably, the image buffer 250 is of sufficient capacity to store at least several seconds' worth of frames of ultrasound scan data. The frames of ultrasound scan data are stored in a manner to facilitate retrieval thereof according to its order or time of acquisition. The image buffer 250 may be embodied as any known data storage medium.

In some instances, the ultrasound system 200 may be configured to support grayscale and color based operations. For example, the signal processor 240 may be operable to perform grayscale B-mode processing and/or color processing. The grayscale B-mode processing may comprise processing B-mode RF signal data or IQ data pairs. For example, the grayscale B-mode processing may enable forming an envelope of the beam-summed receive signal by computing the quantity $(I^2+Q^2)^{1/2}$. The envelope can undergo additional B-mode processing, such as logarithmic compression to form the display data.

The display data may be converted to X-Y format for video display. The scan-converted frames can be mapped to grayscale for display. The B-mode frames that are provided to the image buffer 250 and/or the display system 260. The color processing may comprise processing color based RF signal data or IQ data pairs to form frames to overlay on B-mode frames that are provided to the image buffer 250 and/or the display system 260. The grayscale and/or color processing may be adaptively adjusted based on user input—e.g., a selection from the user input device 230, for example, for enhance of grayscale and/or color of particular area.

In some instances, ultrasound imaging may include generation and/or display of volumetric ultrasound images— that is where objects (e.g., organs, tissues, etc.) are displayed three-dimensional 3D. In this regard, with 3D (and similarly 4D) imaging, volumetric ultrasound datasets may be acquired, comprising voxels that correspond to the imaged objects. This may be done, e.g., by transmitting the sound waves at different angles rather than simply transmitting them in one direction (e.g., straight down), and then capture their reflections back. The returning echoes (of transmissions at different angles) are then captured, and processed (e.g., via the signal processor 240) to generate the corresponding volumetric datasets, which may in turn be used in creating and/or displaying volume (e.g. 3D) images, such as via the display 250. This may entail use of particular handling techniques to provide the desired 3D perception.

For example, volume rendering techniques may be used in displaying projections (e.g., 2D projections) of the volumetric (e.g., 3D) datasets. In this regard, rendering a 2D projection of a 3D dataset may comprise setting or defining a perception angle in space relative to the object being displayed, and then defining or computing necessary information (e.g., opacity and color) for every voxel in the dataset. This may be done, for example, using suitable transfer functions for defining RGBA (red, green, blue, and alpha) value for every voxel.

In various implementations, the ultrasound system 200 may be configured to support new data storage and management scheme for medical imaging solutions, as described in this disclosure. For example, once the imaging data is obtained or generated, the signal processor 240 (and/or components thereof, such as the data management module 242) may store the processed image in the archive 270, which may be configured to, independently or under control of signal processor 240 (and/or components thereof, such as the data management module 242), apply archiving based encoding (e.g., DICOM based encoding) to the data, and then apply separation process as described herein, for storage and management, including performing required communication functions for transmitting the resultant data objects to corresponding storage locations (local or remote). The archive 270 may also be configured to delivers the data back, and such may be configured to perform the recovery process, including on-the-fly recovery. In this regard, the archive 270 may be configured to apply the recovery process to previously archived data, including performing required communication functions for requesting and receiving the corresponding data objects to from storage locations (local or remote), and to decode the data to enable generating corresponding images, such as for display via the display system 260. These functions may be controlled or managed by the signal processor 240 (and/or components thereof, such as the data management module 242). Alternatively, the archive 270 may also be configured to perform at least some of these functions independently, and as such the processor 240 may not be even know that the data underwent any separation. In some instances, the processor 240 (and/or components thereof, such as the data management module 242) may handle data in accordance with the scheme—e.g., being configured to retrieve metadata and blob separately, to further improve the response time and throughput.

Figure 3:
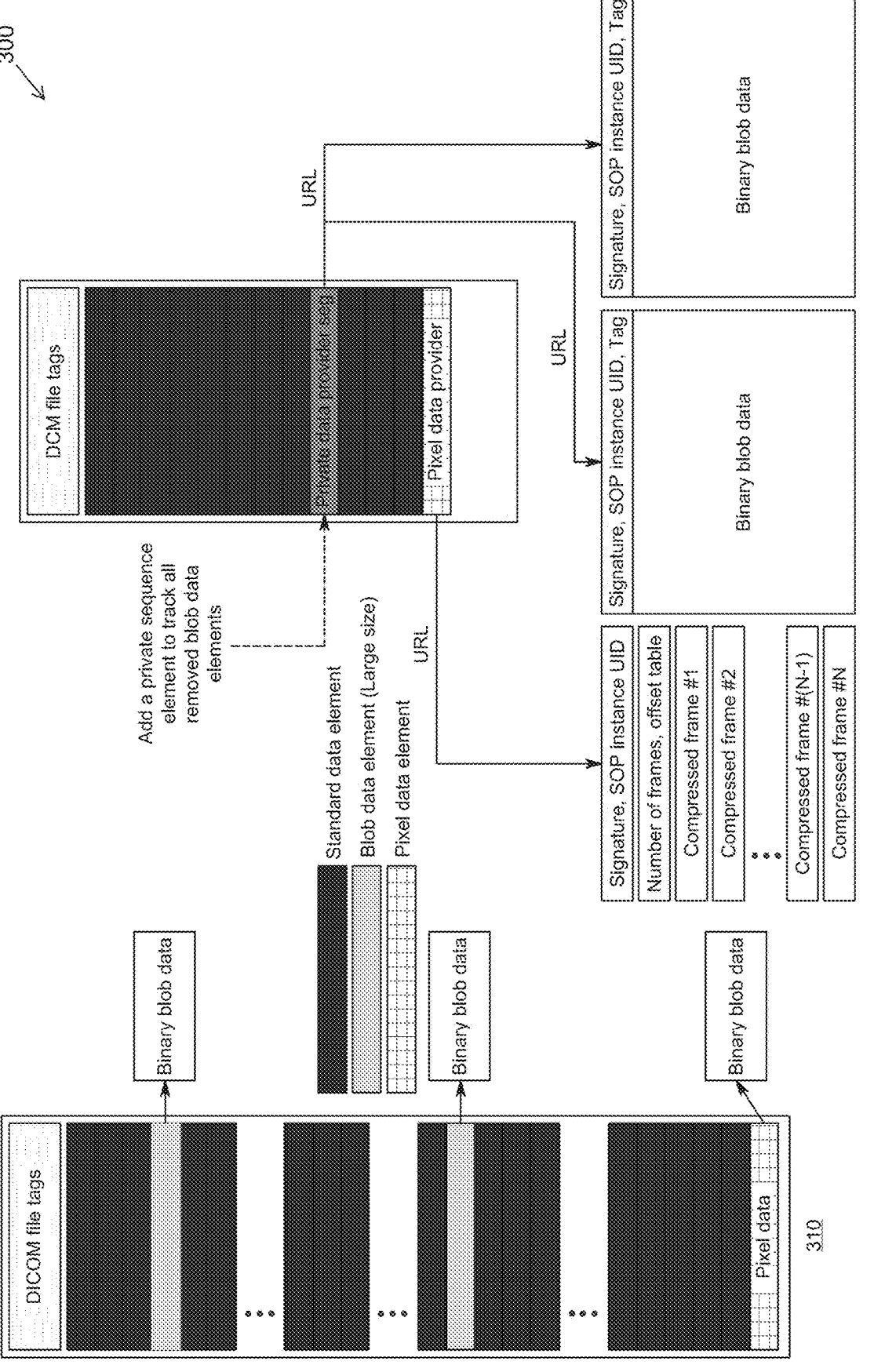
FIG. 3 illustrates an example process for metadata separation for use in new data storage and management scheme for medical imaging solutions.

FIG. 3 illustrates an example process for metadata separation for use in new data storage and management scheme for medical imaging solutions. Shown in FIG. 3 is block diagram 300 illustrating use of the new data storage and management scheme with Digital Imaging and Communications in Medicine (DICOM) based data structure.

In this regard, while the new data storage scheme is applicable to many types of medical data (e.g., images, waveforms, clinical observations, etc.), which may be modeled as a collection of attributes, such as to represent the captured examination, measurement, observation, and monitoring data and its subject and clinical context, FIG. 3 illustrates an example application of the new data storage scheme to a DICOM Service Object Pair (SOP) instance, to explain how the new data storage scheme works.

As shown in FIG. 3, in accordance with the new data storage scheme the DICOM based data blob may be separated into metadata and blob data parts. In this regard, while DICOM header and pixel data may be split in some existing solutions, specifically as internal storage format, the separating applied to the data blob in accordance with the new data storage scheme entail more than that. In particular, in accordance with the new data storage scheme, using open industry standards, all data files may be structured according to standard formats and therefore independently verifiable, and linked together, such as using Uniform Resource Identifiers (URIs), such as Uniform Resource Identifiers (URLs). These translate into high degree of data integrity and resilience, enormously increased data management and storage flexibility, improved performance and higher productivity. We'll discuss some possible new use cases in the following text.

With respect to separation of data blob into parts of metadata and blob data, on the top level, instead of handling a DICOM SOP instance as a whole data blob, image pixel data (any other binary data if desired) and any other large size tags (both standard and private tags) may be removed and saved into separate data files. The resultant object is referred to hereinafter as DICOM SOP instance metadata. Thus, each DICOM SOP instance is split to one metadata object (denoted "D (meta)") and 0-N blob data object(s), where data may be image pixel data or other binary large size data tag contents (denoted "D (blob)").

The separation process, and the objects generated based thereon, may have various useful properties which may enable more efficient and/or otherwise-new data management and arhciving paradigms. Such propocritics may including, for example: 1) The D (meta) may contain subject and clinical context information about D (blob), and most consumer applications usually need access D (meta) first, before deciding whether they need blob data. 2) The D (meta) and D (blob) may have different natures, such as in terms of data management and access availablity—e.g., D (meta) may be subject to modifications (e.g., subject information reconciliation, study/series structure re-organization) and may require very fast response to access, whereas D (blob) may be perfectly immutable, and may be emphasized with high throughput in terms of access. 3) The D (meta) may be full Protected Health Information (PHI) data and therefore extremely sensitive information, whereas D (blob) without D (meta) may be much less PHI. Nonetheless, this does not necessarily suggest any of these objects are not PHI; rather, the level of sensitivity may be different, which maybe important consideration, particularly in a hybrid cloud, distributed storage infrastructure. 4) The size (e.g., in megabytes (MBs)) of D (meta) may be dramatically smaller than the size of D (blob). For example, size ratio of D (meta) relative to D (blob) may be 100 or higher. The separation scheme allows for making use of these properties, to optimize access performance, storage efficiency and high security standards without trade-off.

An example metadata separation process is illustrated in FIG. 3, in which binary standard tag (e.g., pixel data) and large size private tag values are removed from an original DICOM SOP instance 310, and saved into separate binary data files. The concrete data structure and URI linking based thereon are also illustrated and are now further explained with reference to FIG. 3 (particularly the right-hand side thereof).

The D (blob) may comprise pixel data or other binary data. For pixel data, be it single frame or multi-frame, the D (blob) may be encoded as a successive list of frames in a binary data file. For example, D (blob) may be encoded using the following format: 1) file signature, 2) a unique identifier (UID) that represents the SOP Instance UID which this blob data file is part of, 3) an offset table of each image frames, relative to the end of the table, successively stored in the file, 4) image frames, frame by frame in the same order they are encoded in the original SOP instance, and 5) image frame data that are stored in compressed byte steam (e.g., in JPEG File Interchange Format (JFIF)) in the same format as the original SOP instance. Compressed frame byte stream has a length of even number of bytes as DICOM sequence item requires. So, padding byte may be included. Storing JFIF stream adds one more data integrity check. Other (generic) binary blob D (blob) may be stored in a binary file in the same byte stream as is in the original SOP instances. For example, in such cases the D (blob) may be encoded using the following format: 1) file signature, 2) a UID that represents the SOP Instance UID which this blob data file is part of, and 3) byte stream of the binary blob data as encoded in the metadata context. Thus, the D (blob) may be a valid DICOM encoded stream, which may be decoded by applying the transfer syntax of the original SOP instance. In an example implementation the file signature may be 4 bytes, the unique identifier (UID) may be 64 bytes, and the offset table may be (N+1) 4-bytes integers, where the first integer value represents the length of the table, followed by offsets of each image frames, relative to the end of the table, successively stored in the file.

The D (meta) may be encoded in DICOM Part 10 file, but with some modifications. For example, the D (meta) may be encoded as such: 1) replacing pixel tag with pixel data provider tag, which contains a URI (e.g., URL) pointing to D (blob) file; 2) removing the values (data) of all large size blob data elements which have been stored in binary blob files (thus one or more D (blob) files may be created); 3) adding one archive-system owned private tag, which is DICOM SQ element, and therefore is able to record multiple pairs of tag path within the SOP Instance and URI(s) to its D (blob); and 4) adding signed signature(s) of D (blob) for protection of data integrity. In an example implementation the file signature may be 4 bytes and the unique identifier (UID) may be 64 bytes.

Recovering original DICOM SOP instances may simply be achieved by performing a reverse operation of the separation process. Such recovery process is illustrated in and described in more detail with respect to FIG. 4.

Figure 4:
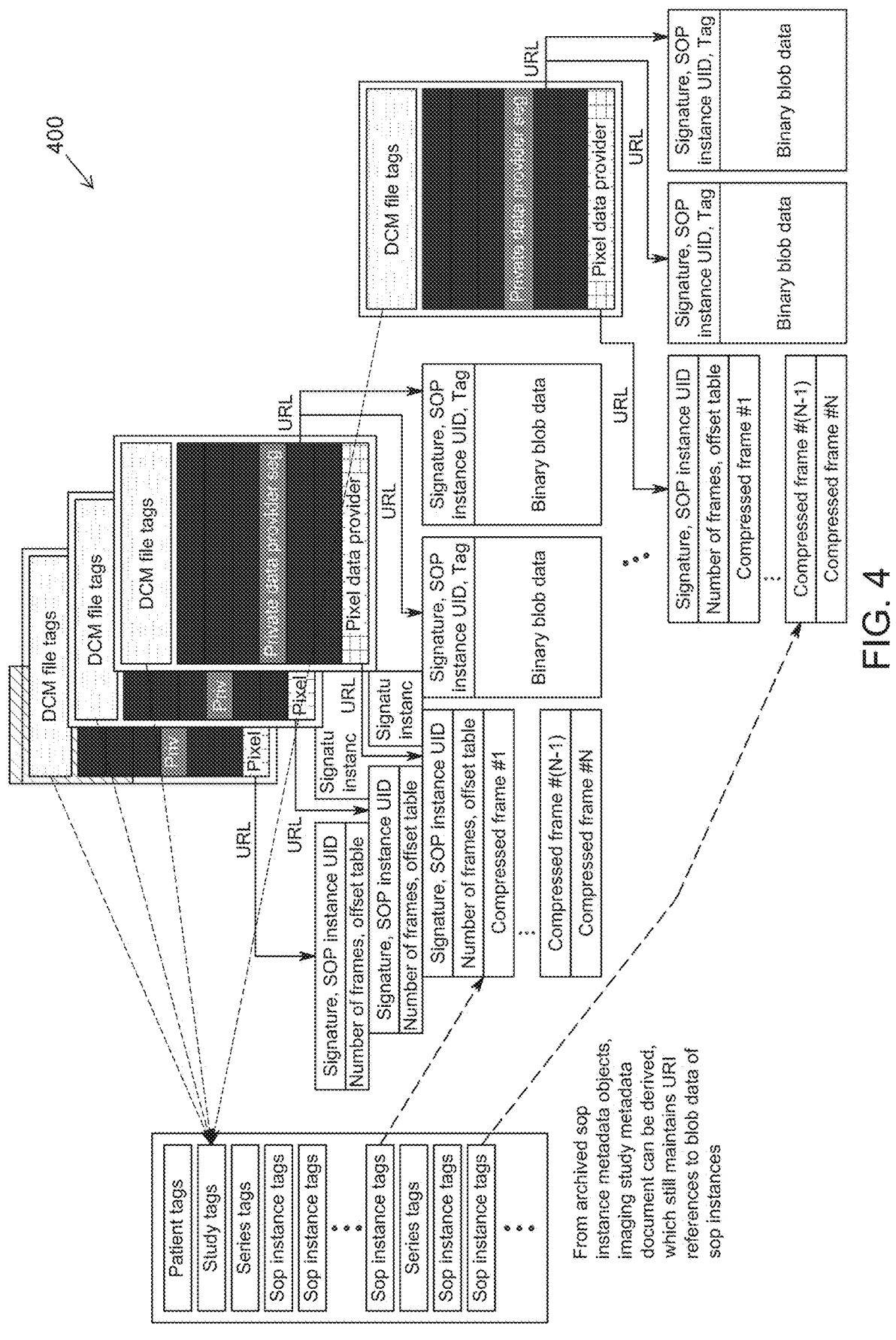
FIG. 4 illustrates an example use scenario for deriving imaging study metadata document from metadata objects.

FIG. 4 illustrates an example use scenario for deriving imaging study metadata document from metadata objects. Shown in FIG. 4 is block diagram 400 illustrating use scenario based on an implementation of the new data storage and management scheme.

Use of the new data storage and management scheme, and data structures generated based thereon, may enable performing various functions that may not be possible or available with existing solutions. For example, various functions may be enabled only based metadata workload, without accessing to blob data objects at all. Imaging study metadata document, for example, may be derived from the metadata objects of each individual DICOM SOP instances of a study, to provide one-stop-shopping for viewer applications, as illustrated in FIG. 4.

In this regard, recovering original DICOM SOP instances may simply be reverse operation of the separation process. In particular, with the signed signature, high standard of data protection may be achieved. For example, additional security measures, including blockchain based ledger, may be used to protect all of D (meta) and D (blob), based on security policy, demands, and available infrastructure. For instance, based on certain access profile configuration, it may be possible to reassemble DICOM SOP instances with or without large size blob data elements to optimize network traffic and data throughput. The bi-direction links between D (meta) and D (blob) further enhance the data integrity.

Viewer applications (e.g., in systems used for analyzing the results of medical imaging) may use the imaging study metadata document to plan DICOM SOP instances presentation, without expensive, multiple queries to the index database. The new storage and management scheme and the separation process based thereon may enable a number of new use cases. Examples of such use cases may include separation of metadata workload and blob data workload for system performance, flexible storage architectures for metadata and blob data, and data protection and security implementations for metadata and blob data.

In an example separation of metadata workload and blob data workload for system performance based use case, standard DICOM API may be supported by reassembling D (meta) and D (blob) into original DICOM SOP instances. The API (e.g., DICOM Web) may be provided to allow access to metadata and blob data separately, which allows much faster access to metadata, even if all images of a large study are retrieved, whereas image pixel data may be accessed on demand. Data management functions may directly modify D (meta) rather than modifying indexed metadata in database, and applying modifications to DICOM SOP instances later. Metadata objects may be loaded into data lake/document query processing engine for data discovery. After a target collection of data objects is located, blob data may be retrieved seamlessly using the URIs in the metadata.

In an example flexible storage architectures for metadata and blob data: Metadata may be stored independently from blob data based use case, metadata is managed on-premises if user desires to do so, but immutable pixel data may be moved to cloud based storage. This allows users to have tight control of context data (metadata) with reduced compute and storage resource demand, while leveraging cloud storage for (almost) contextless data (blob data). More efficient massive data access as well as export. For example, for research or AI model training usage, an archive may be set up with de-identified metadata, sharing immutable blob data managed in a separated store with operational archive. Metadata may be deployed at edges (may be replicated), while Blob Data is archived in deep storage, to achieve both response time and throughput goals.

In an example data protection and security implementations for metadata and blob data based use case, metadata and blob data may be handled with different security measures best satisfying the underlying storage mechanism as well as business needs. For example, blob data archived in public cloud may be audit trailed in blockchain ledger, and user-selected keys may be used to encrypt metadata in their own data center.

Figure 5:
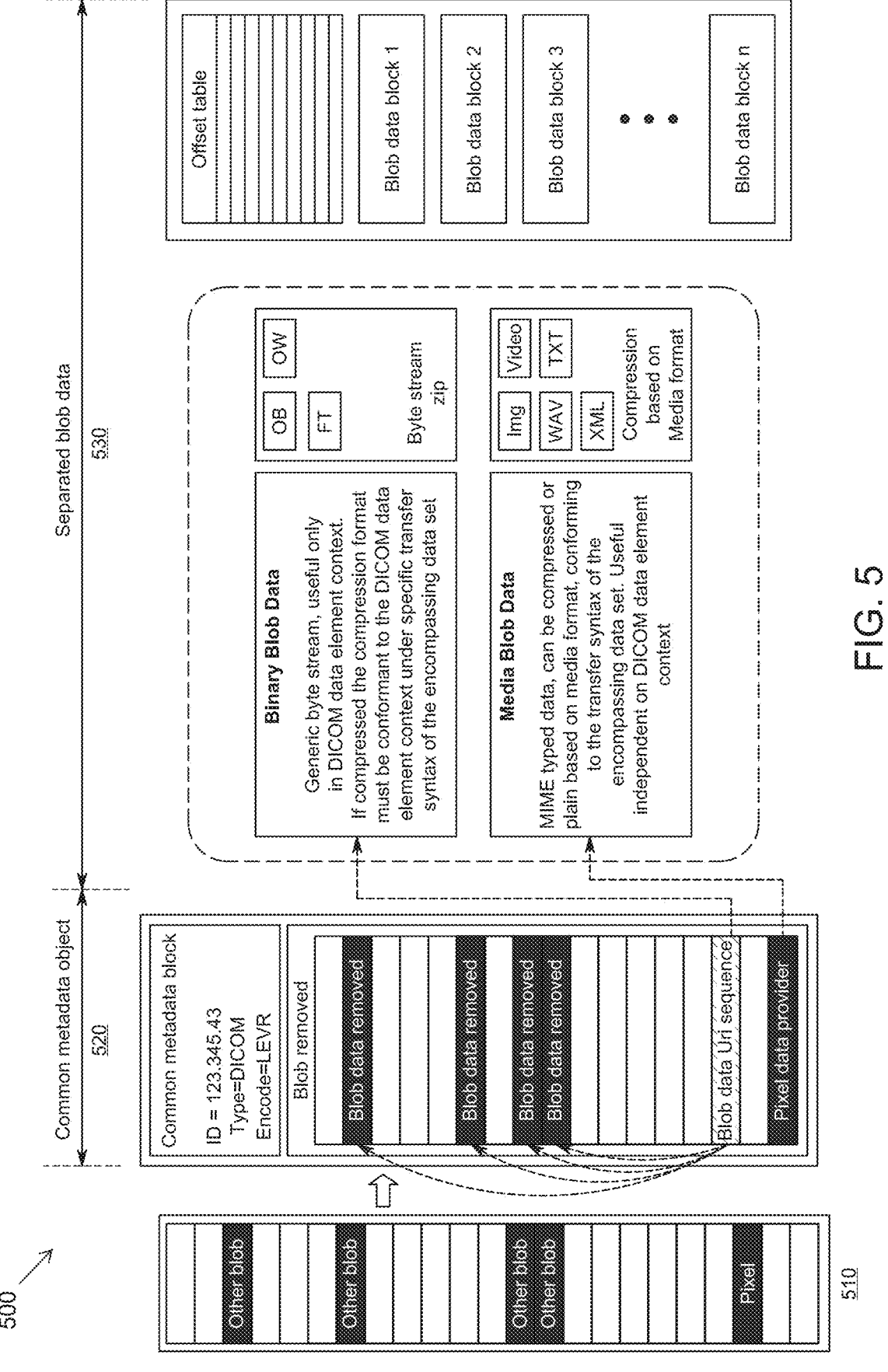
FIG. 5 illustrates an example use scenario for separation of Digital Imaging and Communications in Medicine (DICOM) based data to blob and metadata objects.

FIG. 5 illustrates an example use scenario for separation of Digital Imaging and Communications in Medicine (DICOM) based data separation to blob and metadata objects. Shown in FIG. 5 is block diagram 500 illustrating an example separation of DICOM dataset 510.

The DICOM dataset 510 may comprise a collection of data elements. As a result of application of separate process as described herein, a common metadata object 520 (e.g., D (meta) as described with respect to FIG. 3) and separated blob data 530 may be generated. In this regard, the separated blob data 530 may comprise, blob data object(s), including binary data and media data, and an offset table, as described above.

With respect to the separation, a threshold may be defined to determine blob elements (denoted "Other Blob" in FIG. 5), data values of which are moved to separate blob data files or objects. The blob elements may remain in metadata, but their values may be set to NULL. A new element for tracking (denoted "Blob Data URI Sequence") may be added, to track these elements and to provide link to the corresponding moved blob data values, such as using URIs. The pixel data element may be directly replaced by a new element (denoted "Pixel Data Provider").

There may be two types of blob data: generic byte stream, which may be useful only with metadata context, and MIME-type accessible data, which may be useful independently from metadata context (e.g., JPEG). In particular, the generic byte stream may be useful only in DICOM data element context. If compressed, the compression format must be conformant to the DICOM data element context under specific transfer syntax of the encompassing dataset. The MIME-type data may be compressed or plain based on media format, conforming to the transfer syntax of the encompassing dataset. Such data may be useful independent of the DICOM data element context.

In some instances, the blob data (and the metadata too) may be further consolidated into larger blob for storage and management efficiency.

Figure 6:
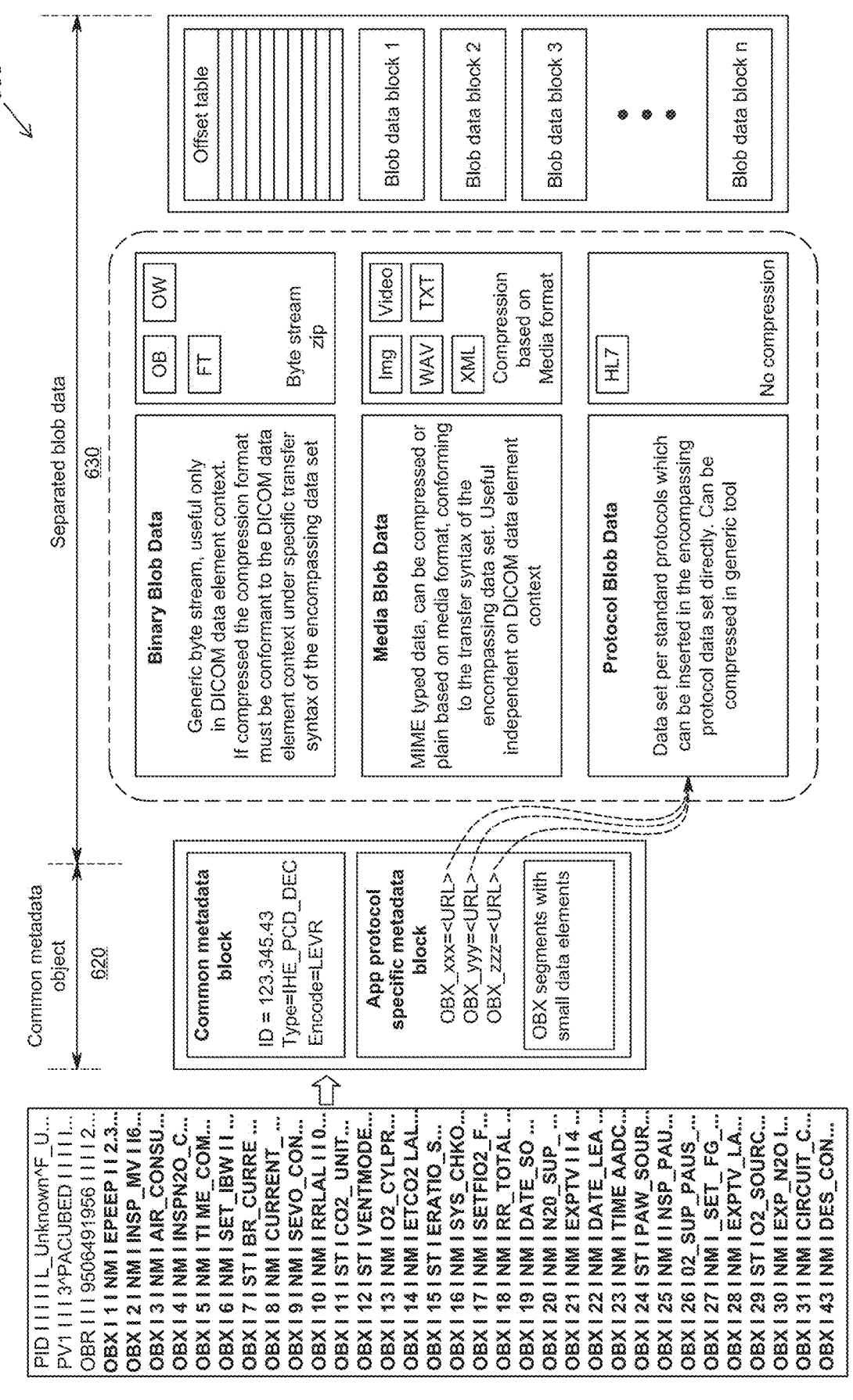
FIG. 6 illustrates an example use scenario for separation of Integrating the Healthcare Enterprise (IHE) Patient Care Device (PCD) Device Enterprise Communication (DEC) based data to blob and metadata objects.

FIG. 6 illustrates an example use scenario for separation of Integrating the Healthcare Enterprise (IHE) Patient Care Device (PCD) Device Enterprise Communication (DEC) based data to blob and metadata objects. Shown in FIG. 6 is block diagram 600 illustrating an example separation of IHE PCD DEC dataset 610.

The IHE PCD DEC dataset 610 may comprise a collection of data elements. As a result of application of separate process as described herein, a common metadata object 620 (e.g., D (meta) as described with respect to FIG. 3) and separated blob data 630 may be generated. In this regard, the separated blob data 630 may comprise, blob data object(s), including binary blob data, media blob data, protocol blob data, and an offset table, as described above.

The separation may be applied in substantially the same manner as described with respect to FIG. 5. In this regard, the binary blob data and the pixel blob data may be substantially similar to the same blob data described with respect to FIG. 5. A third type of blob data is added in the separation process as applied to the IHE PCD DEC dataset 610, namely protocol blob data which may comprise application protocol formatted data block (e.g., Health Level Seven (HL7) formatted data segment), which may be useful only in metadata context, and parsed according to underlying application protocol. Such dataset per standard protocols may be inserted in the encompassing protocol dataset directly, and it may be compressed in generic tool.

In some instances, the blob data (and the metadata too) may be further consolidated into larger blob for storage and management efficiency.

Figure 7:
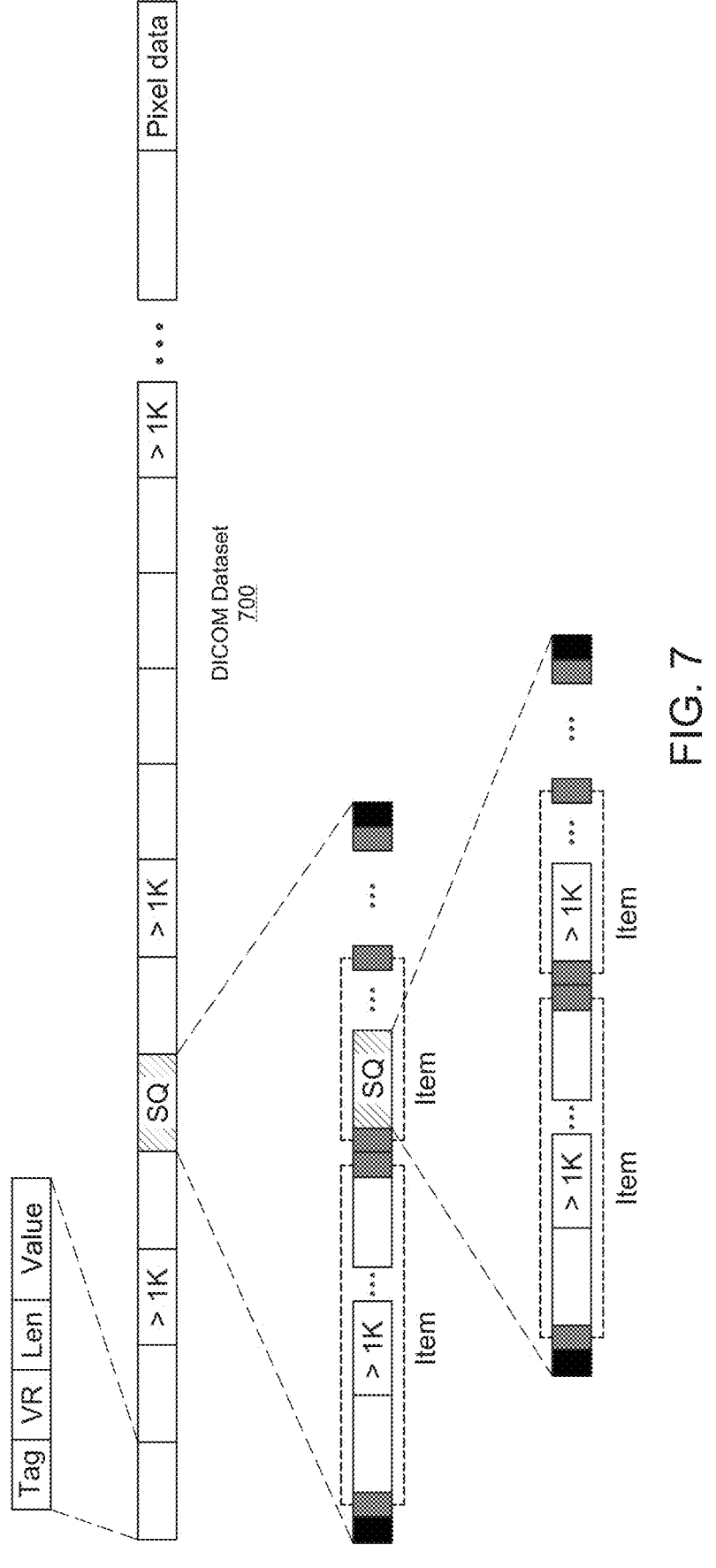
FIG. 7 illustrates an example Digital Imaging and Communications in Medicine (DICOM) based encoded dataset.

FIG. 7 illustrates an example Digital Imaging and Communications in Medicine (DICOM) based encoded dataset. Shown in FIG. 7 is DICOM dataset 700.

The DICOM dataset 700 is a collection of data elements. Each data element may comprise and/or be specified with such fields as tag, value type (VR), value length, and value. If the value type (VR) of a data element is "SQ" (indicating sequence), that data element contains a number of items. In this regard, each item, having start and end marks, may actually be an ordinary DICOM dataset, consisting in turn of a collection of data elements. Data element within an item of a sequence (at one level) may be SQ too, and this may contain a number of items (at a next level), as illustrated in FIG. 7.

Figure 8:
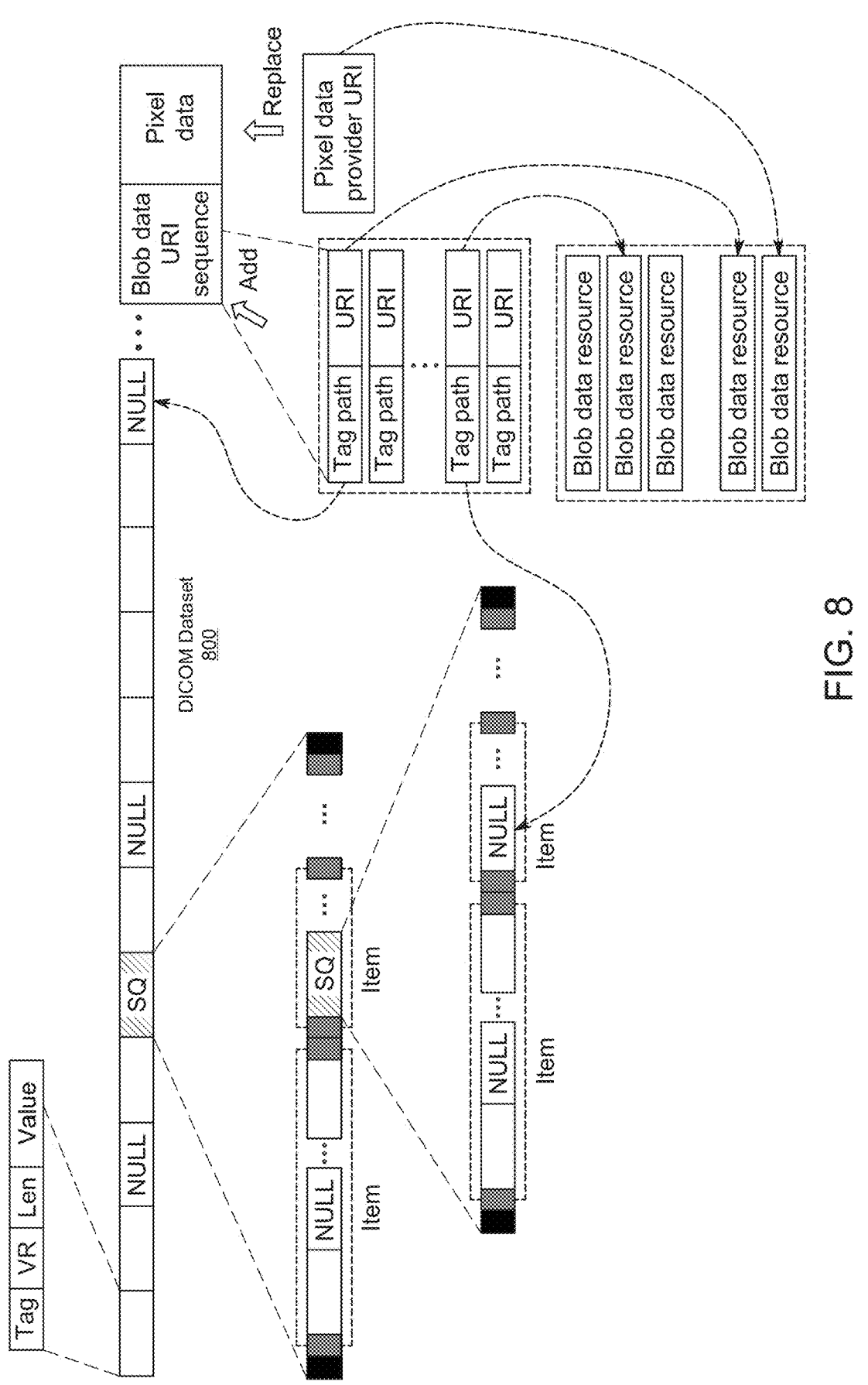
FIG. 8 illustrates an example Digital Imaging and Communications in Medicine (DICOM) based encoded dataset after separation of blob data to blob and metadata objects.

FIG. 8 illustrates an example Digital Imaging and Communications in Medicine (DICOM) based encoded dataset after separation of blob data to blob and metadata objects. Shown in FIG. 8 is DICOM dataset 800, subsequent to application of separation process thereto in accordance with the present disclosure. In this regard, the DICOM dataset 800 may be similar to the DICOM dataset 700 of FIG. 7 prior to the application of the separation process. The separation process may be applied as described above, particularly with respect to FIGS. 3 and 5.

As shown in FIG. 8, subsequent to application of the separation process, all identified blob data elements may remain in the dataset but the value field of each of these blob data elements may be set to NULL. Further, to reflect the change to the value, the value length for each of these blob data elements may be set to '0'. However, the tag and value type (VR) fields, as well as the positions of the blob data elements within the dataset, remain unchanged. The binary values of the blob data elements may be saved in separated files, retrievable via uniform resource identifier (URIs), such as Uniform Resource Locators (URLs). A new sequence element (denoted "Blob Data URI Sequence") is added to track NULL-valued blob elements and locations of their actual values. For example, Blob Data URI Sequence may comprise a list of elements, each comprising two fields: a "tag path" field to track location of particular NULL-valued blob element in the dataset, and a URI pointing to location where the actual value of the NULL-valued blob element is stored. The pixel data element is also replaced with pixel data provider URI, as described above.

FIG. 9 illustrates flowcharts of example separation and recovery processes based on the new data storage and management scheme in accordance with the present disclosure.

Shown in FIG. 9 is flow charts 900 and 950, each comprising a plurality of example steps (represented as blocks 902-912 and 952-962), which may be performed in a suitable system (e.g., the medical imaging system 110 and/or the computing system 120 of FIG. 1) for, respectively, separating and retrieving imaging dataset based on the new data storage and management scheme for medical imaging solutions.

With respect to flow chart 900, in start step 902, the system may be setup, and operations may initiate. In step 904, archiving encoding (e.g., DICOM, IHE PCD DEC, etc.) may be applied to imaging data. In this regard, the imaging data may be generated in the same system or may be obtained from another system. In step 906, blob elements in encoded dataset may be identified. This may be done, for example, by use of threshold. The threshold may be predefined, or alternatively it may be set or adjusted by the operator. In step 908, metadata and blob data objects may be generated and/or updated, based on the identified blob elements. This may comprise, for example, moving value (data) of identified blob elements to separate blob data objects (including, in some instances, of different types, such as byte blob data, media blob data, protocol blob data, etc.). This step may also comprise updating remaining fields in identified blob data elements (e.g., setting value to NULL, adding links to data objects, etc.), adding new fields/elements (e.g., Blob Data Uri Sequence, Pixel Data Provider element, etc.). In step 910, the Store metadata and blob data objects (locally and/or remotely). In step 912, offset table may be generated and/or updated.

With respect to flow chart 950, in start step 952, the system may be setup, and operations may initiate. In step 954, required blob elements in encoded dataset may be identified. In this regard, in some instances, the whole of the dataset may be needed, thus necessitating value (data) of all blob elements in the dataset. However, in other instances, the dataset may be used in more selective manner, such as when only some of the previously obtained images (or portions thereof) may be needed for viewing (or examination). Thus, only some of the blob elements in the dataset may be required and hence recovered. In step 956, the identified blob elements may be processed. This may comprise assessing fields in these blob elements, to determine where the value (data) thereof is maintained (e.g., directly within dataset or in data object). For example, where the value is set to NULL, the location of the real value may be determined, such using the URIs and/or the offsets table. In step 958, Retrieve values for identified blob elements maintained separate from dataset from—this may be done using URIs and offset table. In step 960, Apply required decoding and decompression. In step 962, imaging data may be (re-) generated based on the value (data) of the dataset or portions thereof.

An example method, in accordance with the present disclosure, for storing and managing medical data (e.g., comprising medical imaging data), comprises applying, by a processor, one or more medical data storage and management based processes, the medical data storage and management based processes comprising at least a separation process and a recovery process, wherein the separation process comprises identifying one or more blob data elements in a medical dataset, moving data of the identified one or more blob data elements into corresponding separated data objects, and generating data for indicating the moving of data of the identified one or more blob data elements and for tracking location of moved data of the identified one or more blob data elements, and the recovery process comprises identifying one or more removed blob data elements in a separated medical dataset, wherein data of the identified one or more removed blob data elements is moved into corresponding one or more separated data objects, and for each removed blob data element of the identified one or more removed blob data elements determining, based on corresponding separation data associated with the separated medical dataset, location of a corresponding separated data object, and retrieving, based on determined location, data of the removed blob data element. The medical dataset may comprise and/or be generated based on medical imaging data obtained during medical imaging operations.

In an example implementation, the separation process further comprises generating a data locator element for tracking moved data, the data locator element comprising mapping data to track each of the identified one or more blob data elements and location information for locating corresponding moved data.

In an example implementation, the separation process further updating each of the identified one or more blob data elements, the updating comprising modifying at least one field to indicate that data of the identified one or more blob data elements is moved.

In an example implementation, the separation process further comprises generating and populating a common metadata block that comprises information relating to the medical dataset, the separation process, and the corresponding separated data objects.

In an example implementation, the separation process further comprises generating and populating an offset table for tracking storage of the separated data objects.

In an example implementation, the separation process further comprises storing moved data of at least some of the separated data objects in different storage locations, the different storage locations comprising one or both of local and remote storage locations.

In an example implementation, the medical dataset comprises Digital Imaging and Communications in Medicine (DICOM) based dataset or Healthcare Enterprise (IHE) Patient Care Device (PCD) Device Enterprise Communication (DEC) based dataset.

An example non-transitory computer readable medium, in accordance with the present disclosure, may have stored thereon, a computer program having at least one code section, the at least one code section being executable by a machine comprising at least one processor, for causing the machine to perform one or more steps for storing and managing medical data (e.g., comprising medical imaging data), comprising applying one or more medical data storage and management based processes, the medical data storage and management based processes comprising at least a separation process and a recovery process, wherein the separation process comprises identifying one or more blob data elements in a medical dataset, moving data of the identified one or more blob data elements into corresponding separated data objects, and generating data for indicating the moving of data of the identified one or more blob data elements and for tracking location of moved data of the identified one or more blob data elements, and the recovery process comprises identifying one or more removed blob data elements in a separated medical dataset, wherein data of the identified one or more removed blob data elements is moved into corresponding one or more separated data objects, and for each removed blob data element of the identified one or more removed blob data elements determining, based on corresponding separation data associated with the separated medical dataset, location of a corresponding separated data object, and retrieving, based on determined location, data of the removed blob data element. The medical dataset may comprise and/or be generated based on medical imaging data obtained during medical imaging operations.

In an example implementation, the separation process further comprises generating a data locator element for tracking moved data, the data locator element comprising mapping data to track each of the identified one or more blob data elements and location information for locating corresponding moved data.

In an example implementation, the separation process further updating each of the identified one or more blob data elements, the updating comprising modifying at least one field to indicate that data of the identified one or more blob data elements is moved.

In an example implementation, the separation process further comprises generating and populating a common metadata block that comprises information relating to the medical dataset, the separation process, and the corresponding separated data objects.

In an example implementation, the separation process further comprises generating and populating an offset table for tracking storage of the separated data objects.

In an example implementation, the separation process further comprises storing moved data of at least some of the separated data objects in different storage locations, the different storage locations comprising one or both of local and remote storage locations.

In an example implementation, the medical dataset comprises Digital Imaging and Communications in Medicine (DICOM) based dataset or Healthcare Enterprise (IHE) Patient Care Device (PCD) Device Enterprise Communication (DEC) based dataset.

An example system, in accordance with the present disclosure, for storing and managing medical data (e.g., comprising medical imaging data), comprises at least one processor configured to apply one or more medical data storage and management based processes, the medical data storage and management based processes comprising at least a separation process and a recovery process, wherein the separation process comprises identifying one or more blob data elements in a medical dataset, moving data of the identified one or more blob data elements into corresponding separated data objects, and generating data for indicating the moving of data of the identified one or more blob data elements and for tracking location of moved data of the identified one or more blob data elements, and the recovery process comprises identifying one or more removed blob data elements in a separated medical dataset, wherein data of the identified one or more removed blob data elements is moved into corresponding one or more separated data objects, and for each removed blob data element of the identified one or more removed blob data elements determining, based on corresponding separation data associated with the separated medical dataset, location of a corresponding separated data object, and retrieving, based on determined location, data of the removed blob data element. The medical dataset may comprise and/or be generated based on medical imaging data obtained during medical imaging operations.

In an example implementation, the separation process further comprises generating a data locator element for tracking moved data, the data locator element comprising mapping data to track each of the identified one or more blob data elements and location information for locating corresponding moved data.

In an example implementation, the separation process further updating each of the identified one or more blob data elements, the updating comprising modifying at least one field to indicate that data of the identified one or more blob data elements is moved.

In an example implementation, the separation process further comprises generating and populating a common metadata block that comprises information relating to the medical dataset, the separation process, and the corresponding separated data objects.

In an example implementation, the separation process further comprises generating and populating an offset table for tracking storage of the separated data objects.

In an example implementation, the separation process further comprises storing moved data of at least some of the separated data objects in different storage locations, the different storage locations comprising one or both of local and remote storage locations.

As utilized herein the terms "circuits" and "circuitry" refer to physical electronic components (e.g., hardware) and any software and/or firmware ("code") which may configure the hardware, be executed by the hardware, and or otherwise be associated with the hardware. As used herein, for example, a particular processor and memory may comprise a first "circuit" when executing a first one or more lines of code and may comprise a second "circuit" when executing a second one or more lines of code. As utilized herein, "and/or" means any one or more of the items in the list joined by "and/or". As an example, "x and/or y" means any element of the three-element set $\{(x), (y), (x, y)\}$. In other words, "x and/or y" means "one or both of x and y." As another example, "x, y, and/or z" means any element of the seven-element set $\{(x), (y), (z), (x, y), (x, z), (y, z), (x, y, z)\}$. In other words, "x, y and/or z" means "one or more of x, y, and z." As utilized herein, the terms "block" and "module" refer to functions than can be performed by one or more circuits. As utilized herein, the term "exemplary" means serving as a non-limiting example, instance, or illustration. As utilized herein, the terms "for example" and "e.g.," set off lists of one or more non-limiting examples, instances, or illustrations. As utilized herein, circuitry is "operable" to perform a function whenever the circuitry comprises the necessary hardware (and code, if any is necessary) to perform the function, regardless of whether performance of the function is disabled or not enabled (e.g., by some user-configurable setting, a factory trim, etc.).

Other embodiments of the invention may provide a non-transitory computer readable medium and/or storage medium, and/or a non-transitory machine readable medium and/or storage medium, having stored thereon, a machine code and/or a computer program having at least one code section executable by a machine and/or a computer, thereby causing the machine and/or computer to perform the processes as described herein.

Accordingly, the present disclosure may be realized in hardware, software, or a combination of hardware and software. The present invention may be realized in a centralized fashion in at least one computing system, or in a distributed fashion where different elements are spread across several interconnected computing systems. Any kind of computing system or other apparatus adapted for carrying out the methods described herein is suited. A typical combination of hardware and software may be a general-purpose computing system with a program or other code that, when being loaded and executed, controls the computing system such that it carries out the methods described herein. Another typical implementation may comprise an application specific integrated circuit or chip.

Various embodiments in accordance with the present disclosure may also be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

While the present invention has been described with reference to certain embodiments, it will be understood by those skilled in the art that various changes may be made and equivalents may be substituted without departing from the scope of the present invention. In addition, many modifications may be made to adapt a particular situation or material to the teachings of the present invention without departing from its scope. Therefore, it is intended that the present invention not be limited to the particular embodiment disclosed, but that the present invention will include all embodiments falling within the scope of the appended claims.

What is claimed is:

1. A method for storing and managing medical data, the method comprising:

applying, by a processor, one or more medical data storage and management based processes, the medical data storage and management based processes comprising at least a separation process and a recovery process, wherein:

the separation process comprises:

identifying one or more blob data elements in a medical dataset;

moving data of the identified one or more blob data elements into corresponding separated data objects; and generating data for indicating the moving of data of the identified one or more blob data elements and for tracking location of moved data of the identified one or more blob data elements, wherein the identified one or more blob data elements reside in a remote storage location comprising diagnostic imaging data that represents a portion of a medical imaging file, and wherein the one or more blob data elements are separated from metadata for the medical dataset that identifies at least one uniform resource identifier (URI) linked to the one or more blob data elements, wherein the one or more blob data elements store binary data, and wherein the at least one URI replaces a pixel-data field of each identified blob data element in the medical dataset; and the recovery process comprises:

identifying one or more removed blob data elements in a separated medical dataset, wherein data of the identified one or more removed blob data elements is moved into corresponding one or more separated data objects; and for each removed blob data element of the identified one or more removed blob data elements:

determining, based on corresponding separation data associated with the separated medical dataset, location of a corresponding separated data object; and retrieving, based on determined location, data of the removed blob data element.

2. The method of claim 1, wherein the separation process further comprises generating a data locator element for tracking moved data, the data locator element comprising mapping data to track each of the identified one or more blob data elements and location information for locating corresponding moved data.

3. The method of claim 1, wherein the separation process further updating each of the identified one or more blob data elements, the updating comprising modifying at least one field to indicate that data of the identified one or more blob data elements is moved.

4. The method of claim 1, wherein the separation process further comprises generating and populating a common metadata block that comprises information relating to the medical dataset, the separation process, and the corresponding separated data objects.

5. The method of claim 1, wherein the separation process further comprises generating and populating an offset table for tracking storage of the separated data objects.

6. The method of claim 1, wherein the separation process further comprises storing moved data of at least some of the separated data objects in different storage locations, the different storage locations comprising one or both of local and remote storage locations.

7. The method of claim 1, wherein the medical dataset comprises Digital Imaging and Communications in Medicine (DICOM) based dataset or Healthcare Enterprise (THE) Patient Care Device (PCD) Device Enterprise Communication (DEC) based dataset.

8. A non-transitory computer readable medium having stored thereon, a computer program having at least one code section, the at least one code section being executable by a machine comprising at least one processor, for causing the machine to perform one or more steps for storing and managing medical data comprising:

applying one or more medical data storage and management based processes, the medical data storage and management based processes comprising at least a separation process and a recovery process, wherein:

the separation process comprises:

identifying one or more blob data elements in a medical dataset;

moving data of the identified one or more blob data elements into corresponding separated data objects; and generating data for indicating the moving of data of the identified one or more blob data elements and for tracking location of moved data of the identified one or more blob data elements, wherein the identified one or more blob data elements reside in a remote storage location comprising diagnostic imaging data that represents a portion of a medical imaging file, the generated data comprising at least one uniform resource identifier (URI) pointing to the remote storage location storing an actual value of the identified one or more blob elements, wherein a pixel data element of the one or more blob data elements is replaced with the at least one URI that represents a pixel data provider URI, and wherein the one or more blob data elements are separated from metadata for the medical dataset that identifies the at least one URI linked to the one or more blob data elements, wherein the one or more blob data elements store binary data, and wherein the at least one URI replaces a pixel-data field of each identified blob data element in the medical dataset; and the recovery process comprises:

identifying one or more removed blob data elements in a separated medical dataset, wherein data of the identified one or more removed blob data elements is moved into corresponding one or more separated data objects; and for each removed blob data element of the identified one or more removed blob data elements:

determining, based on corresponding separation data associated with the separated medical dataset, location of a corresponding separated data object; and retrieving, based on determined location, data of the removed blob data element.

9. The non-transitory computer readable medium of claim 8, wherein the separation process further comprises generating a data locator element for tracking moved data, the data locator element comprising mapping data to track each of the identified one or more blob data elements and location information for locating corresponding moved data.

10. The non-transitory computer readable medium of claim 8, wherein the separation process further updating each of the identified one or more blob data elements, the updating comprising modifying at least one field to indicate that data of the identified one or more blob data elements is moved.

11. The non-transitory computer readable medium of claim 8, wherein the separation process further comprises generating and populating a common metadata block that comprises information relating to the medical dataset, the separation process, and the corresponding separated data objects.

12. The non-transitory computer readable medium of claim 8, wherein the separation process further comprises generating and populating an offset table for tracking storage of the separated data objects.

13. The non-transitory computer readable medium of claim 8, wherein the separation process further comprises storing moved data of at least some of the separated data objects in different storage locations, the different storage locations comprising one or both of local and remote storage locations.

14. The non-transitory computer readable medium of claim 8, wherein the medical dataset comprises Digital Imaging and Communications in Medicine (DICOM) based dataset or Healthcare Enterprise (IHE) Patient Care Device (PCD) Device Enterprise Communication (DEC) based dataset.

15. A system for storing and managing medical data, the system comprising:

at least one processor configured to apply one or more medical data storage and management based processes, the medical data storage and management based processes comprising at least a separation process and a recovery process, wherein:

the separation process comprises:

identifying one or more blob data elements in a medical dataset;

moving data of the identified one or more blob data elements into corresponding separated data objects; and generating data for indicating the moving of data of the identified one or more blob data elements and for tracking location of moved data of the identified one or more blob data elements, wherein the identified one or more blob data elements reside in a remote storage location comprising diagnostic imaging data that represents a portion of a medical imaging file, the generated data comprising at least one uniform resource identifier (URI) pointing to the remote storage location storing an actual value of the identified one or more blob elements, wherein a pixel data element of the one or more blob data elements is replaced with the at least one URI that represents a pixel data provider URI, and wherein the one or more blob data elements are separated from metadata for the medical dataset that identifies the at least one URI linked to the one or more blob data elements, wherein the one or more blob data elements store binary data, and wherein the at least one URI replaces a pixel-data field of each identified blob data element in the medical dataset; and the recovery process comprises:

identifying one or more removed blob data elements in a separated medical dataset, wherein data of the identified one or more removed blob data elements is moved into corresponding one or more separated data objects; and for each removed blob data element of the identified one or more removed blob data elements:

determining, based on corresponding separation data associated with the separated medical dataset, location of a corresponding separated data object; and retrieving, based on determined location, data of the removed blob data element.

16. The system of claim 15, wherein the separation process further comprises generating a data locator element for tracking moved data, the data locator element comprising mapping data to track each of the identified one or more blob data elements and location information for locating corresponding moved data.

17. The system of claim 15, wherein the separation process further updating each of the identified one or more blob data elements, the updating comprising modifying at least one field to indicate that data of the identified one or more blob data elements is moved.

18. The system of claim 15, wherein the separation process further comprises generating and populating a common metadata block that comprises information relating to the medical dataset, the separation process, and the corresponding separated data objects.

19. The system of claim 15, wherein the separation process further comprises generating and populating an offset table for tracking storage of the separated data objects.

20. The system of claim 15, wherein the separation process further comprises storing moved data of at least some of the separated data objects in different storage locations, the different storage locations comprising one or both of local and remote storage locations.

* * * * *